United States Patent [19]
Goepp et al.

[11] 4,369,219
[45] Jan. 18, 1983

[54] CUSTOM VALVED CERVICAL CAP WITH DEFORMABLE MARGIN

[75] Inventors: Robert A. Goepp, Chicago; Uwe E. Freese, Oak Park; Marvin P. Loeb, Chicago, all of Ill.

[73] Assignees: University Patents, Inc., Norwalk, Conn.; Contracap, Inc., Schaumburg, Ill.

[21] Appl. No.: 163,328

[22] Filed: Jun. 26, 1980

[51] Int. Cl.³ .......................... B32B 3/10; A61F 5/46
[52] U.S. Cl. .................................... 428/138; 128/127;
128/131; 128/132 R; 128/138 R; 428/156;
428/157; 428/167; 428/172; 428/192; 428/194;
428/195; 428/203; 428/213; 428/215; 428/515;
428/516; 428/517; 428/521; 428/139
[58] Field of Search .............. 428/138, 192, 194, 157,
428/161, 203, 213, 215, 139, 156–172, 195, 515,
516, 517, 521; 128/127, 132 R, 138 R

[56] References Cited
U.S. PATENT DOCUMENTS

| | | | |
|---|---|---|---|
| 2,836,177 | 5/1958 | Sells | 128/127 |
| 2,851,032 | 9/1958 | Friedman | 128/127 |
| 3,952,737 | 4/1976 | Lipfert | 128/127 |
| 4,007,249 | 2/1977 | Erb | 128/127 |
| 4,322,463 | 3/1982 | Goepp | 428/138 |

*Primary Examiner*—Ellis P. Robinson

[57] ABSTRACT

A non-invasive birth control device in the form of a custom-formed, valved cervical cap is disclosed. The cervical cap comprises a cup-shaped elastomeric shell substantially complementary with contiguous surface of portio vaginalis cervicis when in contact therewith, having an aperture at the apex of the shell, and a depending skirt that is thinner than said shell and is provided with a plurality of spaced slits. The aperture is covered by an elastomeric web secured to the shell and defines, together with the shell, a one-way valve means having a discharge port offset from the aperture. The cervical cap can be fabricated from a specially designed blank of a thermoplastic elastomeric material using a replica of cervix uteri as a mold.

25 Claims, 13 Drawing Figures

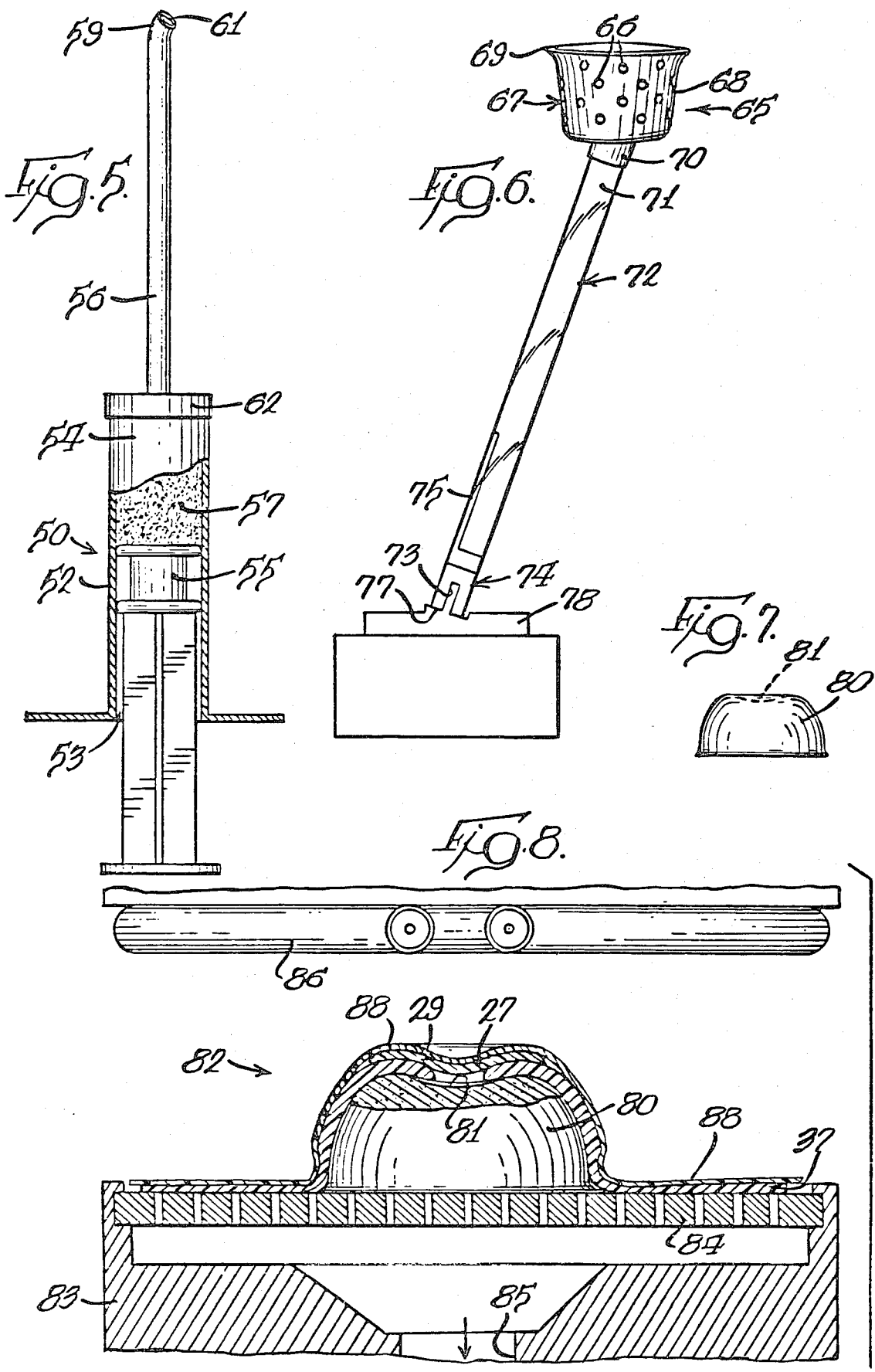

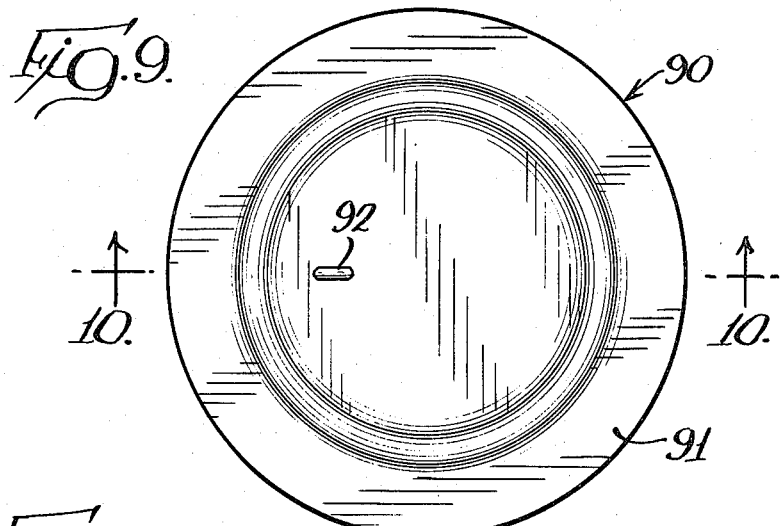
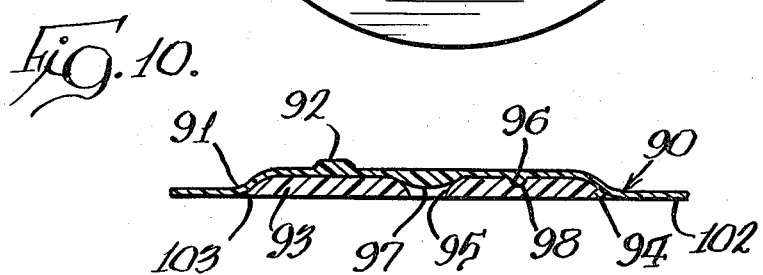
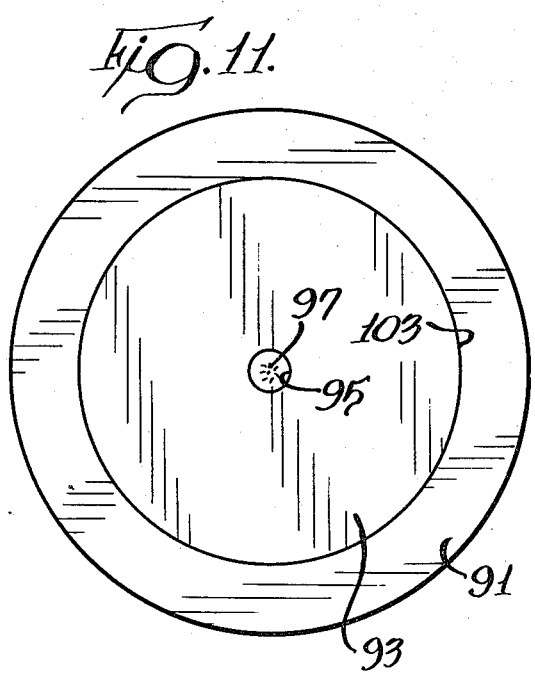
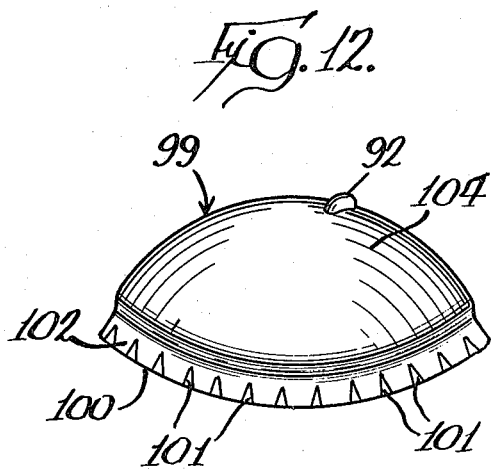

CUSTOM VALVED CERVICAL CAP WITH DEFORMABLE MARGIN

TECHNICAL FIELD

This invention relates to contraceptive devices and means for making such devices.

BACKGROUND OF THE INVENTION

Caps for cervix uteri as a birth control means have been known for a long time and have been found among the artifacts of antiquity. It has been reported that Aetius of Amida suggested for this purpose the use of a pomegranate shell cut into a hollow cup, and that beeswax discs fashioned to fit over the cervix have been used in Europe.

Modern cervical caps comprise a pre-formed rubber cap that is positioned over the cervix uteri to act as a sperm barrier. Such caps are manufactured in several sizes to accommodate the various uterine sizes normally encountered; however, with such caps the fit for a particular individual is inexact and necessarily a compromise. As a result, these caps often become dislodged during coitus and have to be removed periodically to accommodate normal uterine discharges. Thus, such caps are inconvenient to use and have not achieved a high degree of reliability.

Premanufactured cervical caps with valves are also known and are shown in U.S. Pat. No. 2,836,177 to Sells, U.S. Pat. No. 3,952,737 to Lippert et al. and German Pat. No. 475,496 to Leopold. These caps also suffer from the aforementioned lack of stability and are subject to dislodgement during use.

U.S. Pat. No. 4,007,249 to Erb describes a technique for custom fabrication of a cervical cap having a valve that is inserted during manufacture. The manufacturing expedients disclosed in this particular patent contemplate the painting of a liquid, polymerizable elastomeric material onto the cervix uteri followed by the polymerization of the painted material or, in the alternative, the use of a mold which retains a liquid, polymerizable elastomeric material in contact with the exocervical surface until it is polymerized.

The former expedient is impractical because the surface to which the liquid, polymerizable material is applied is wet with mucus and quite slippery, thus the applied material would fall off the exocervical surface due to gravity before polymerization of the material could take place and, in any event, it would be impossible to control the thickness of the applied polymerizable material during in situ polymerization. A cervical cap having a relatively non-uniform thickness is undesirable, however, because it is unstable and is likely to be dislodged in use. The second expedient disclosed in the Erb patent would also produce caps having an undesirable variable cap thickness that is likely to bring about dislodgement.

A further shortcoming of the caps shown in the Erb patent is that the prefabricated valving means utilized are of the leaflet or flap type. In such valves a viscous droplet of cervical mucus could hold the valve in an open position for an undesirably long time period, thereby providing an access aperture for sperm and defeating the very purpose of the cap. Moreover, inasmuch as the polymerizable material of the cap is in a fluid state when it surrounds the prefabricated valve, some of the fluid material may become enmeshed with the valve and interfere with its intended valving action after the material has polymerized.

U.S. Pat. No. 4,007,249 to Erb also mentions a technique disclosed initially by F. A. Wilde in 1838 in Das Weibliche Gebär-Unvermögen according to which a cervical cap allegedly can be made from a special wax impression of the vaginal portion of the cervix. As recognized by Erb, such a technique cannot produce an identical, negative-image, cervix-conforming inside surface because the cervix would be deformed while the wax impression is being made. The uterus is suspended in the lower abdomen by ligaments, is easily movable, and would tend to move up into the abdomen even with a gentle force applied to the cervix. As a result, accurate registration would be prevented by such a movement with attendant lack of stability for the cervical cap produced in such manner.

The techniques described by Erb are also likely to suffer from the same drawback, albeit for a different reason. In particular, in practicing these techniques the vaginal wall has to be expanded using a vaginal speculum or similar implement in order to expose the cervix during cap molding. This expedient tends to distort the cervix as well, elongating it along an imaginary line between the tips of the inserted, open vaginal speculum blades and shortening the cervix along an imaginary line at right angles to the imaginary line between the tips of the speculum blades. The attendant cervical distortion exceeds the limits for prosthetic stability of the cervical cap that is produced.

Accordingly, while a stable, well-fitting cervical cap can be an effective birth-control device, prior to the invention described and claimed in copending U.S. patent application U.S. Ser. No. 108,319, filed on Dec. 31, 1979 now U.S. Pat. No. 4,322,463 it was not possible to produce a cervical cap that has the requisite stability against dislodgement and that can be worn for extended periods of time such as months, or even years, without removal. The present application discloses a further refinement of the aforementioned invention that enhances the stability of a cervical cap.

SUMMARY OF INVENTION

The present invention, in one aspect, contemplates a non-invasive birth control device in the form of a removable cervical cap provided with a deformable margin such as a depending, independently deformable skirt portion. The cap is custom made and comprises a form-fitting apertured, elastomeric shell portion in which the aperture is situated in communication with the external os of cervix uteri when in place and is covered with an elastomeric web portion conforming and secured to the shell portion and, together with the shell portion, defining a one-way valve means and a channel having a discharge port offset from the aperture. An integral skirt portion, thinner than the shell portion, depends therefrom and is provided with a plurality of slits extending from the peripheral edge of the skirt portion in a direction toward the apex of the shell portion.

A preferred embodiment of the cap includes a cup-shaped elastomeric shell having a convex outer surface and a concave inner surface that is substantially complementary with contiguous surface of portio vaginalis cervicis when in contact therewith. The shell defines an aperture at the apex thereof. An elastomeric web positioned over the aperture conforms with and is secured to the outer surface of the shell so as to define a channel therebetween and in communication with the aperture.

The web coacts with the shell outer surface so as to provide a one-way valve which accommodates the flow of uterine discharges entering the aperture. The channel terminates in a discharge port that is off-set from the aperture and preferably is situated at or near the peripheral edge of the shell. That portion of the shell surrounding the aperture may be beveled to provide an increased valve seat area contiguous with the overlying portion of the web and also to facilitate fabrication of the cap.

The shell of the cap has a depth sufficient to receive a major portion of the portio but the periphery of the shell terminates short of fornices vaginae. The integral skirt portion is flexible and may extend up to or into the fornices, however.

Preferably the shell has at least a band of substantially uniform rigidity circumscribing the portio and in contact therewith. More preferably this band of substantially uniform rigidity is a band of substantially uniform shell thickness covering the entire area of the prominent portion of the cervix surrounding the external os thereof, i.e., the cervical eminence around the external os. It is also preferable that the peripheral edge of the shell is feathered, i.e., tapered or beveled from the outer surface of the shell toward the shell periphery.

The custom cervical cap embodying the present invention can be conveniently formed from an elastomeric blank using a replicated cast of cervix uteri. The blank comprises a substantially planar sheet of a thermoplastic elastomeric material defining a central aperture therein and an elastomeric web superposed over the aperture and secured to the planar sheet about the aperture so as to provide a one-way passageway from said aperture between the web and the sheet. Peripheral margin of the blank has a thickness that is less than the thickness of the planar sheet in the region of the sheet that defines the central aperture.

In one embodiment of this invention the blank comprises a substantially planar sheet of an elastomeric thermoplastic material, having an embossed region or land of substantially uniform thickness surrounded by a planar region having a thickness that is less than the thickness of the embossed region. A central aperture of the type described hereinabove is provided in the embossed region or land of the blank. The elastomeric web, having a thickness less than the thickness of the embossed region sheet, is superposed over the aperture and is secured to the embossed region of the sheet, usually about the major portion of the aperture periphery, defining a pocket or channel which provides a one-way fluid passageway extending from the aperture, between the web and the sheet, and to a discharge port defined by the sheet and an unsealed or free edge portion of the web.

The custom cervical cap can also be formed utilizing a composite blank that is constituted by a relatively thicker planar sheet of an elastomeric thermoplastic material and a relatively thinner planar elastomeric web that is superposed over the relatively thicker planar sheet and extends beyond the periphery of the latter. A central aperture is provided in the planar sheet. The aperture is covered on one side of the planar sheet by the elastomeric web which is intermittently attached to the planar sheet to define between the sheet and the web a channel or channels which provide a one-way fluid passageway extending from the aperture to the periphery of the planar sheet.

The cervical cap contemplated by the present invention can be fabricated by first making an impression of the exocervical surface of cervix uteri in the vagina in a substantially undistorted, relaxed state, making a replica of the protruding portion of cervix uteri, molding the cervical cap utilizing a blank of the aforementioned type, and then trimming away excess material and forming a plurality of spaced slits in the deformable skirt portion of the cap. The slits can be straight cuts, inverted V-shaped notches, or the like.

The valved cervical cap embodying the present invention is a non-invasive and entirely passive birth control device. The cap does not interfere with the normal hormonal balance of the individual wearer and thus avoids the side effects commonly encountered with hormonal contraceptives.

Inasmuch as the cap is not placed within a human body like an intrauterine device but, instead, is positioned on the exocervical surface of cervix uteri, it does not have to be sterilized. Likewise, no foreign body reaction and attendant rejection are encountered.

The cap may be worn for extended periods of time. No preplanning, anticipation, or periodic attention is needed. Thus, there is no interference with the spontaneity of sexual activity. Additionally, the presence of the cap may protect the cervix, uterus and Fallopian tubes from undesirable external influences and infections.

The cap embodying this invention can be fabricated in a relatively short time period, of the order of about five minutes, using a replicated cast of the prospective user's cervix uteri. Little technical skill is required for fabrication.

The one-way valve included in the present cap provides the further advantages of reliability and increased sperm travel distance in the unlikely event that sperm does enter the space between the web and the shell, since the possible sperm entry region is distant from the shell aperture. The normal cyclical changes in the viscosity of cervical mucus do not affect the efficacy or the barrier characteristics of the valve. In contradistinction to the previously known leaflet or flap-type valves which could be held open by a viscous droplet of cervical mucus, the present valve design causes droplet-like cervical mucus descending from the cervical os to flatten out into a very thin film, which does not hold open the valve itself.

BRIEF DESCRIPTION OF THE DRAWINGS

In the drawings,

FIGS. 5 and 6 illustrate devices suitable for practicing the present invention;

FIG. 7 is a side elevational view showing a cast replica of the cervix of female uterus;

FIG. 8 is an enlarged sectional elevational view illustrating the manufacture of a cervical cap in accordance with the present invention;

FIG. 9 is a plan view showing another type of blank suitable for fabricating a cervical cap embodying the present invention;

FIG. 10 is a sectional view taken along plane 10—10 in FIG. 9;

FIG. 11 is a bottom view of the blank shown in FIG. 9; and

FIG. 12 is an enlarged perspective view of a valved cervical cap embodying the present invention and fabricated from the blank shown in FIGS. 9-11, inclusive.

DESCRIPTION OF PREFERRED EMBODIMENTS

Figure 1:
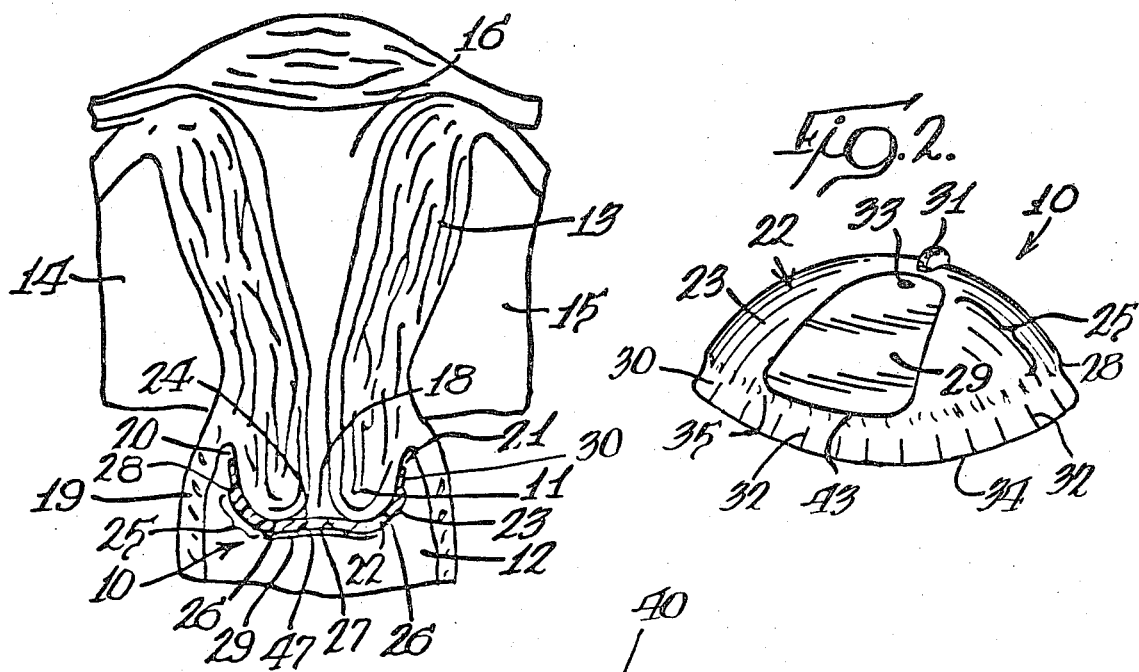
FIG. 1 is an elevational view, partly in section, of a portion of the internal organs of the female reproductive system with a cervical cap embodying the present invention in place.

Referring to FIG. 1, valved cervical cap 10 is shown positioned on the exocervical surface of cervix uteri 11, i.e., on the portio vaginalis cervicis or that portion of uterus 13 that protrudes into vagina 12. Uterus 13 is supported by broad ligaments 14 and 15, and defines fundus 16 that terminates in cervical os 18. Vaginal wall 19 and cervix 11 together define the fornices vaginae, i.e., lateral fornices 20 and 21 as well as the anterior and posterior fornices (not shown).

Cap 10 is comprised by a cup-shaped elastomeric shell or shell portion 22 having convex outer surface 23 and concave inner surface 24. Surface 26 of the portio vaginalis cervicis is not distorted by cap 10 and is in mating contact with concave inner surface 24 at least along band 25 of shell 22 which is of substantially uniform rigidity. In the area of contact, concave inner surface 24 is substantially complementary with the contiguous surface 26 of the portio vaginalis cervicis. Preferably the thickness of shell 22 is substantially uniform, at least along peripheral band 25, for optimum stability of cap 10 when in place. Also, it is preferred that the band of substantially uniform thickness constitutes a major portion of shell 22. Flexible skirt portion 30 provides a deformable margin that depends from shell 22 and is substantially thinner than the thickness of peripheral band 25, i.e., no more than about one-half the thickness of band 25.

Skirt portion 30 can be unitary with shell 22 or can be made from a separate strip of the same or different elastomeric material secured to shell 22 at the peripheral edge thereof by heat sealing, adhesive bonding, ultrasonically, or in any other convenient manner. At the juncture of shell 22 and skirt portion 30, edge portion 28 of shell 22 is featured, i.e., beveled or tapered, so as to provide a relatively smooth, gradual transition from one material thickness to another.

Figure 2:
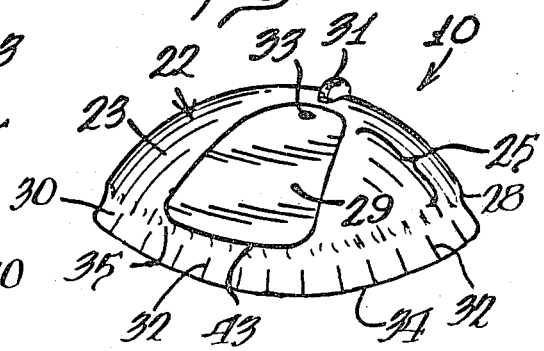
FIG. 2 is an enlarged perspective view of a valved cervical cap embodying the present invention.

Aperture 27 is provided in elastomeric shell 22 at the apex thereof and, as shown in FIG. 1, is positioned adjacent to cervical os 18 when cap 10 is in place. An external cover for aperture 27 is provided by elastomeric web or web portion 29 that is integral with shell 22. Web 29 is secured to shell 22 about a major portion but not the entirety of its periphery so as to provide an unsecured or free edge portion (FIG. 2) that together with adjacent surface portion of convex surface 23 defines a discharge port or external opening 43. As shown in FIG. 2, web 29 covers only a portion of shell 22; however, web 29 can also cover the entire external surface of shell 62.

Web 29 lies against shell 22 and substantially conforms to the contour thereof. In some instances web 29 may also be under tension and/or biased against convex surface 23. Web 29 and the covered portion of outer surface 23 together define a channel or pocket that communicates with aperture 27 and forms a one-way valve extending from aperture 27, between web 29 and surface 23, an defining discharge port 43 in a direction away from the apex of shell 22, and thus spaced from aperture 27. Preferably the defined discharge port is situated at least about one aperture diameter away from aperture 27, and more preferably, is situated near or at shell periphery 35, i.e., at or near the junction of shell 22 and skirt portion 30.

This one-way valve opens under increased uterine pressure and permits the passage of fluids such as mucus, menstrual flow, and the like from fundus 16 to vagina 12 without disturbing the positioning of cervical cap 10 and without permitting the entry of sperm into fundus 16. Additionally, the precise fit of cervical cap 10 onto the portio permits mucus to flow around it; however, at the same time the forces generated by the flow and surface tension of mucus assist in orienting and in holding cap 10 firmly in place.

As best seen in FIG. 2, flexible skirt portion 30 is provided with a plurality of spaced slits 32 that begin at peripheral edge 34 of skirt portion 30 and which can extend toward the apex of shell 22 substantially at right angles to peripheral edge 34. Slits 32 may extend substantially across the entire width of skirt portion 30 or may terminate short of beveled portion 28 of shell 22. In one preferred embodiment of this invention the slits extend at least one-half the width of the skirt portion. The spacing between adjacent slits depends on the flexibility of the skirt portion and may vary in the range of about 2 millimeters to about 10 millimeters. More preferably slits 32 are spaced about 4 to about 6 millimeters apart and are at least about 1.5 millimeters long.

As further shown in FIG. 2, optionally cap 10 can be provided with an integral tactile orientation marker 31 for the purpose of facilitating orientation of cap 27 upon insertion, as well as enabling the wearer to periodically assure herself that cap 10 remains properly positioned. Marker 31 can be an upstanding projection as shown, or a depression such as a dimple that is discernible to touch. Visual indicia 33 may also be provided on elastomeric web 29 in some instances for the purpose of facilitating the locating of aperture 27 underneath web 29 during manufacture of cap 10 as will be described in detail hereinbelow.

Shell 22 is dimensioned so as to have a depth sufficient to receive a major portion of the portio as illustrated in FIG. 1; however, periphery 35 of shell 22 terminates short of the fornices vaginae so as to guard against dislodgement of cap 10 during activity that may cause uterus 13 to shift position and/or to deform or distend the normal configuration of the fornices. To avoid dislodgement of the cap during momentary, severe uterine displacement it is important that peripheral edge 35 is sufficiently elastic to remain in contact with the exocervical surface contiguous therewith even during such momentary uterine displacement. For optimum retention of the cap, it is desirable to maximize the contact area between the cap and the exocervical surface. To this end, skirt portion 30 integral with shell 22 performs a very useful function in that further contact area is provided. Additionally, the relatively thin cross-section of flexible skirt portion 30, and slits 32, permit a localized deformation of skirt portion 30 upon uterine displacement or distortion without a material reduction in the contact area available for cap retention.

Cap 10 preferably is positioned on cervix uteri 11 so that discharge port or external opening 43 of the valve defined by web 29 in conjunction with convex outer surface 23 of shell 22 is located in or near the posterior fornix and also at a location on surface 23 that is closer to shell periphery 35 than to the apex of the shell, and thus to the apex of cap 10. In the embodiment illustrated in FIG. 2 discharge port 43 is substantially coincidental with shell periphery 35, preferably is situated no more than about 1 to about 3 millimeters from shell periphery 35. If desired, web 29 may extend also beyond shell periphery 35 up to peripheral edge 34 of skirt portion 30. This results in a manifold increase in the distance that sperm deposited in the vagina must travel to reach cervical os 18.

A portion of the increased distance for sperm travel is in vertical 12 where the environment is very inhospitable to sperm motility due to the relatively low ambient pH. Usually sperm can survive in the vaginal vault only for a time period of about one to two hours. Inasmuch as sperm can move at a velocity of about one to two millimeters per minute, the substantial increase in the distance that sperm must travel with cap 10 in place alone markedly reduces the likelihood of sperm survival and ultimate fertilization. Sperm travel to cervical os 18 via the valve means in cap 10 is possible only in close proximity to the walls defining the valve means. Inasmuch as at least shell 42, and preferably both shell 22 and web 29 are of a thermoplastic elastomeric material, which materials exhibit an inhibitory effect on sperm motility, the likelihood of sperm reaching cervix uteri 11 is further reduced.

Shell 22 as well as skirt portion 30 can be made of a wide variety of thermoplastic elastomeric materials, the so-called thermoplastic elastomers, such as polyolefin blends, styrene/elastomer block copolymers, copolyesters, and polyurethane block copolymers. While these thermoplastic elastomers differ chemically, their morphology is similar. Blocks or domains of relatively hard thermoplastic constituents link elastomeric constituents in a network that behaves like a chemically crosslinked rubbery structure. At forming temperatures the relatively hard thermoplastic domains of the structure soften and allow the polymeric material to flow. Upon cooling, these relatively hard domains resolidify and re-establish the rubber-like, elastic structure.

Thermoplastic elastomers that exhibit a surface charge provide a further advantage for the present purposes in that the presence of such a charge on the fabricated shell and/or web tends to inhibit sperm motility.

For purposes of the present invention, the materials particularly suitable for the shell and the skirt portion depending therefrom are the styrene/elastomer block copolymers such as those commercially available from the Shell Chemical Company, Oak Brook, Ill., under the designation "Kraton" and "Kraton G" and described in U.S. Pat. No. 3,231,635 to Holden et al. These styrenic thermoplastic elastomers are block copolymers of polystyrene and an elastomer such as polyisoprene, polybutadiene, ethylene-propylene, or ethylene-butylene rubber.

While thermoplastic elastomeric materials of varying hardness may be used to fabricate shell 22, for optimum stability against dislodgment preferably the material should be harder than the cervical tissue that comes in contact therewith, yet the hardness should not be so high as to cause discomfort to the wearer or her consort. Preferably the shell material, i.e., the material of embossed or thicker region of the blank, has a Shore A durometer hardness value of about 35 to about 70, and more preferably of about 45 to about 60.

The material of construction for the shell and the skirt portions of the cap can be opaque, semi-transparent or transparent; however, for ease of handling or positioning during manufacture of the cervical cap a transparent or clear material is preferred. The materials of construction for the shell and the skirt portions can also be different and can have different physical properties.

Web 29 can be made from the same elastomeric material or from a different elastomeric material, as long as web 29 can be secured to shell 22. For ease of manufacture it is preferred to have web 29 of the same elastomeric material as the shell material but thinner. The shell-to-web thickness ratio usually is about 7:1 to about 3:1 and preferably the average shell-to-web thickness ratio is about 5:1. In a typical cervical cap embodying the present invention the shell thickness is about 1.5 millimeters and the web thickness is about 0.3 millimeters.

The relative thickness of the shell and the integral web in each instance depend on a variety of factors such as the manufacturing procedure, forming temperatures, modulus of elasticity, and the like considerations. In general, however, the web thickness is selected so as to provide a valve-opening pressure of about 10 to about 15 millimeters of mercury for the one-way valve formed by the coaction of web 29 with the outer surface 23 of shell 22 contiguous therewith.

The material for web 29 need not be thermoplastic as long as it exhibits the desired elasticity and can be secured to shell 22. Not only heat sealing or ultrasonic bonding but other bonding means, e.g., adhesive bonding, can be utilized as well. In addition to the aforementioned thermoplastic elastomers, the web portion of the present valved cervical cap can be made from materials such as natural rubber, silicone rubber, polyurethanes, fluorocarbon rubbers, styrene-butadiene rubbers, and the like.

Figure 3:
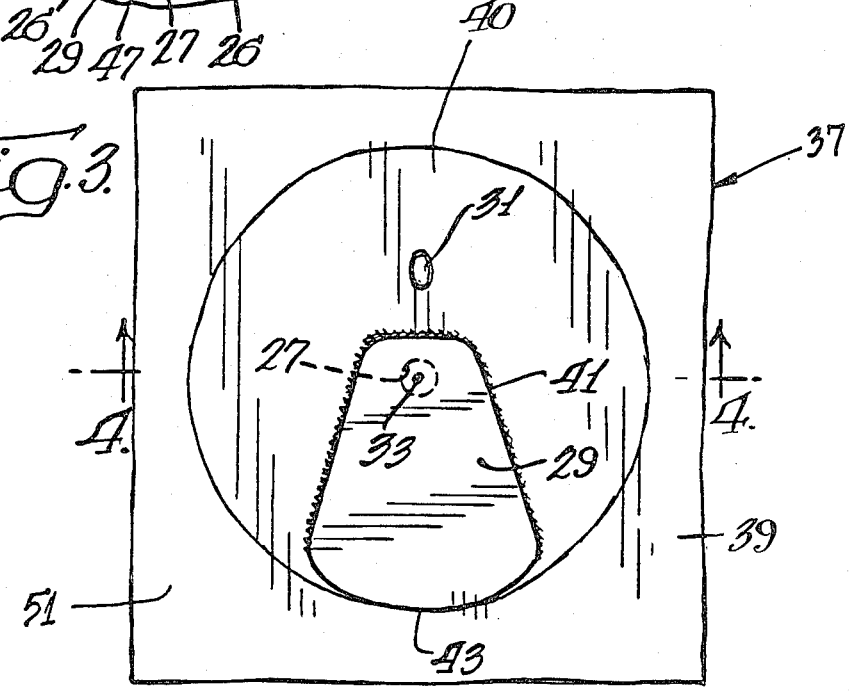
FIG. 3 is a plan view of a blank suitable for fabricating a cervical cap embodying this invention.
Figure 4A:
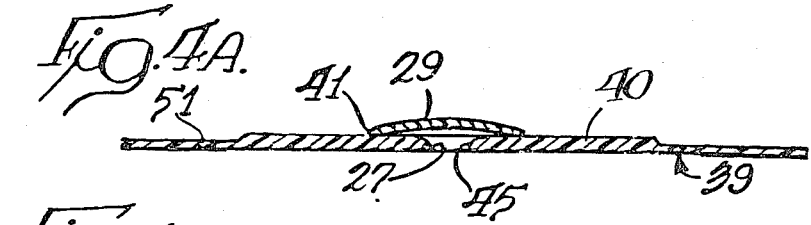
FIG. 4A is a sectional view taken along plane 4—4 in FIG. 3.

Valved cervical cap 10 embodying the present invention can be fabricated by molding a blank of the type shown in FIGS. 3 and 4A wherein blank 37 comprises substantially planar sheet 39 of elastomeric material. Sheet 39, in turn, comprises a central embossed region or land 40 of generally circular configuration from which shell 22 is formed surrounded by a relatively thinner region 51 from which skirt portion 30 is ultimately formed. Typically the central embossed region is about 1 to about 2 millimeters thick and the planar surrounding region is about 0.2 to about 0.4 millimeters thick, i.e., the surrounding, relatively thinner region has a thickness that is no more than about one-half of the thickness of the embossed region. Preferably the thickness ratio of the embossed region to the planar surrounding region is about 3:1 to about 7:1. Typically, the embossed region or land 40 has a diameter of about 25 millimeters to about 50 millimeters. Aperture 27 in the central region of sheet 39 is covered by elastomeric web 29. The contour of web 29 is not critical and can be generally fan-like, bell-shaped, trapezoidal, or circular, for example, as long as the web substantially conforms to the molded shell after the cap has been fabricated and defines a channel terminating at the distal end thereof in a discharge port that can accommodate the uterine discharges.

Web 29, in turn, is secured to sheet 39, e.g., by bonding peripheral region 41 thereof. The securement of web 29 to sheet 39, and thus ultimately to cap 10, is sufficient to permanently attach web 29 to sheet 39 but provides an unsealed, i.e., free, edge portion which serves to define, in part, external valve opening or discharge port 43. In essence, web 29, when secured to sheet 39, defines a pocket or pockets communicating with underlying aperture 27 and provides a one-way passageway or channel between web 29 and that portion of sheet 39 which ultimately becomes a web-covered portion of the convex outer surface 23 for cap 10, terminating in discharge port 43 that is situated at least one aperture diameter away from aperture 27. Preferably the cross-sectional area of the defined passageway increaases with increasing distance from aperture 27 as measured along convex surface 23 of shell 22. Thus, in case of a bell- or fan-shaped web, for instance as shown in FIG. 3, the bonded peripheral region 41 extends about the major portion of the periphery of aperture 27 and the maximum cross-sectional area for the defined passageway is at discharge port 43. The diameter of aperture 27 is usually about 5 to about 10 millimeters.

Aperture 27 can be a through-aperture with rectangular edges, if desired. However, during fabrication, a relatively thin, thermoplastic, elastomeric web may be drawn or forced into aperture 27 too far and may be excessively deformed or even perforated at the line of contact with a rectangular, sharp edge defining aperture 27. The use of such relatively thin webs, if desired, is facilitated if the aperture-defining edge portion of embossed region 40 adjacent to web 29 is beveled as at 45 in FIG. 4A or rounded as at 47 in FIG. 1. In this manner the likelihood that web 29 may be perforated or unduly distorted during fabrication is reduced. The thickness ratio of the embossed region to the overlying web preferably is about 7:1 to about 3:1, and more preferably is about 5:1. Tactile orientation marker 31 is positioned adjacent to a sealed juncture of web 29 and sheeet 39.

Figure 4B:
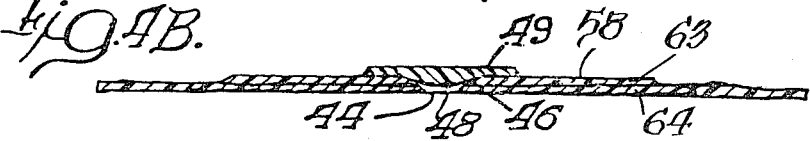
FIG. 4B is a sectional view similar to that in FIG. 4A but showing an alternate cross-sectional configuration for the valve means in a cervical cap of this invention.

An alternate, suitable one-way valve configuration utilizing a relatively thin web is illustrated in FIG. 4B. In this particular embodiment, aperture 44 in composite thermoplastic elastomeric sheet 42 forming the blank is covered by web 49 having unitary protuberance 48 extending into aperture 44 and contacting beveled surface 46 which provides an annular contact surface or valve seat for protuberance 48. That is, web 49 is thicker in the region of aperture 44 and projects into the aperture. When a custom, valved cervical cap is fabricated using a cap blank of the type shown in FIG. 4B, protuberance 48 will abut beveled surface 46 and thus not only will provide a larger sealing area but also, in the case of a relatively thin web, will prevent excessive deformation of the web itself during fabrication. Composite thermoplastic elastomeric sheet 42 is a laminate of two compatible yet dissimilar material layers 63 and 64 selected to provide the desired rigidity and hardness for the shell and the desired flexibility for the skirt portion of the cap. The embossed region or land 58 in the blank derived from composite sheet 42 is provided by a substantially circular thermoplastic elastomer layer 63 superposed over and bonded to underlying layer 64.

It should be noted, however, that even in the case of a substantially uniformly thick web some deformation into the shell aperture, such as aperture 27 (FIGS. 1, 3 and 8), is not objectionable as long as web integrity is not impaired. Such deformation, as best seen in FIG. 8, also can provide a unitary protuberance that projects into the aperture, conforming to the opposite bevel of aperture 27, and enhances the valving action. In addition, the web may be relatively thicker in the region overlying the aperture.

In some instances, particularly when sheet 39 is relatively thick, e.g., of the order of about 2.5 millimeters or more, it is desirable to extend bevel 45 on the aperture edge portion substantially to the juncture 41 of sheet 39 and web 29 so as to provide a substantially uniform thickness throughout. Alternatively, or in addition, the region surrounding aperture 27 and covered by web 29, in the region between juncture 41 and aperture 27 may be countersunk or thinned out, i.e., debossed, for the same purpose.

A prefabricated blank of the foregoing type offers the substantial advantages of ease of custom cap fabrication by a practitioner associated with the practicing physician or with a medical laboratory. Another type of blank suitable for present purposes is shown in FIGS. 9 through 11 and will be described in greater detail hereinbelow.

For optimum fit, concave inner surface 24 of cap 22 is substantially complementary with the surface of the portio vaginalis cervicis contiguous therewith. While it is desirable that concave inner surface 24 projects slightly toward cervical os 18 about the periphery of aperture 27, i.e., has local convexity in the aperture region complementary to the concavity of the cervix in the region surrounding cervical os 18, no portion of surface 24 enters cervical os 18. To this end, the cervix in its normal, undistorted configuration is first replicated as a rigid mold, e.g., in plaster, and the obtained replica is then utilized to mold the cervical cap.

Initially an impression of cervix uteri is made using a physiologically tolerable, hardenable paste. Suitable for this purpose is an aqueous paste made from dental impression powder, e.g., using an algin derivative, usually an alginate such as sodium alginate.

The cervical impression can be made utilizing the implements shown in FIGS. 5 and 6. Syringe 50, shown in FIG. 5, includes hollow body portion 52 having an open end 53 and opposed dispensing end 54 that terminates into elongated nozzle 56 in communication with hollow body portion 52. Plunger 55 is positioned within hollow body portion 52 and is adapted to dispense the syringe contents through nozzle 56. Impression paste 57, e.g., aqueous alginate paste, is contained within hollow body portion 52. To facilitate the distribution of impression paste 57 over the cervix during the course of making the impression, it is preferable to have a nozzle the distal end 59 of which is offset from the longitudinal axis of the nozzle itself. In this manner nozzle discharge port 61 is situated in a plane that is at an acute angle, preferably at an angle of about 45 degrees, with respect to the longitudinal axis of nozzle 56, and can dispense impression paste 57 laterally over the cervix in all directions by simply rotating syringe 50. In an alternate manner, nozzle 56 can be rotatably mounted on syringe body 52 by means of nozzle-bearing hub 62 that is rotatable with respect to syringe body 52.

Preparatory to making a cervical impression as contemplated by the present invention, vagina 12 is expanded using a vaginal speculum so as to expose the cervix. Thereafter impression tray 65 (FIG. 6) is inserted through the speculum and into the vagina, and positioned so that hollow cup 67 thereof envelops the cervix. Cup 67 has a flexible, preferably transparent, wall 68 made from an elastomeric material such as silicone rubber, polyurethane, or the like, that terminates in a peripheral, outwardly flared, anterior lip 69 the purpose of which is to keep out adjacent vaginal wall. Wall 68 and lip 69 are also designed so as to trap the cervix and to prevent its upward rotation with attendant closure of the anterior fornix space when the patient is in a supine position while the cervical impression is made.

Flexible wall 68 is further provided with a plurality of spaced perforations such as perforation 66. Cup 67 at the bottom thereof is provided with a bottom aperture surrounded by posterior sleeve 70. Proximal end 71 of hollow, elongated stem 72 is received within sleeve 70. Stem 72 defines a passageway that communicates with the interior of cup 67. A pair of opposed mounting notches, such as notch 73, are provided in distal end 74 of stem 72. Also at or near distal end 74 marker means 75 is provided on stem 72 for indicating a preselected orientation of cup 67.

While cup 67 and stem 72 can be coaxial, for ease of manipulation and insertion during the making of a cervical impression, and also to facilitate the entrapment of the cervix, it is preferred that the longitudinal axes of cup 67 and stem 72 intersect at an included angle of about 15 to about 25 degrees, and more preferably about 20 degrees.

To make a cervical impression once tray 65 is appropriately positioned enveloping the cervix, nozzle 56 is inserted through hollow stem 72. Preferably, length of nozzle 66 is selected so as to extend for substantially the length of stem 72. More preferably distal end 59 projects into cup 67 through the bottom aperture thereof but remains spaced from the cervix. Hub 62 (FIG. 5) on syringe, upon abutting open end 77 of stem 72, provides a positive stop that prevents nozzle aperture 61 from coming in contact with the cervix. In instances where nozzle 56 is longer than stem 72, appropriate stop means can be provided on nozzle 56 itself or within stem 72 at the proximal end 71 received within sleeve 71.

Impression paste 57 is then dispensed from syringe 50 and distributed so as to cover the cervix, and speculum is removed from the vagina without removing tray 65, and the paste is permitted to set with the cervix in its natural, undistorted shape. The length of stem 72 is selected long enough to permit the easy removal of the speculum without disturbing the position of tray 65. As the impression paste fills cup 67, minor amounts of the paste exude through perforations 66 and, upon setting, anchor the formed impression within tray 65.

After the paste has set, usually within about 90 seconds, tray 65 together with the cervical impression contained therewithin is lifted from the cervix and placed onto vibrating table 78 for casting a replica of the cervix.

The casting operation entails pouring a slurry of plaster of Paris, or like casting material, into tray 65 while the latter is vibrated to permit any trapped air to rise to the surface and to assure that each and every crevice of the formed impression is filled with the slurry. After the slurry has hardened, replica 80 (FIG. 7) is removed from tray 65 and is ready for use in fabricating cervical cap 10.

To this end vacuum molding techniques, e.g., drape forming, can be readily utilized; however, any other molding technique can be utilized as long as the material to be molded can be made to conform closely to the cervical replica, for example, by means of positive air pressure. For purposes of illustration a preferred vacuum molding technique will be described in detail hereinbelow.

Referring to FIG. 8, vacuum molding apparatus 82 comprises base 83 that supports foraminous plate 84 and heat source 86, e.g., a calrod heating element or infrared lamp, in a spaced relationship relative to plate 84. Alternatively, heat can be supplied by a stream of hot air. In the case of a radiant heat source, such as an infrared lamp, the heat-radiating surfaces can be contoured so as to provide a substantially uniform distance between the heat source and the blank portion nearest thereto. Channel 85 in base 83 communicates with a vacuum source (not shown) and permits vacuum to be drawn through plate 84.

Replica 80 is positioned on plate 84 and blank 37 positioned thereover so that visual indicia 33 is superposed over cervical os region 81 of replica 80. A release agent, e.g., an aerosol spray of lecithin commercially available under the designation "Pam" from Boyle-Midway, Inc., New York, N.Y. 10017, is applied to the exposed surface of blank 37, and between the web and the underlying sheet and the blank is then covered with thin protective sheet 88, e.g., a polyethylene terephthalate film, or the like. Preferably sheet 88 is perforated in order to facilitate the vacuum forming operation. Heat source 85 is then turned on and heat applied to blank 37 until it begins to soften and conform to replica 80 by its own weight. Thereafter the vacuum source is turned on and vacuum drawn through foraminous plate 84 so as to press softened sheet firmly against replica 80. Heat source 86 is then turned off or removed, and the formed sheet is permitted to cool while vacuum is maintained. Once cooled and set to a permanent contour, blank 37, now deformed from the original planar configuration, is removed from replica 80, and the formed cervical cap is excised therefrom and the skirt portion thereof trimmed to the desired width. The skirt width, i.e., the distance between the junction of the shell and the skirt on one hand and the peripheral edge of the skirt on the other, depends on the depth of the fornices in any given instance, but usually is about 3 to about 7 millimeters. The specific shell depth in each instance will depend on the contour of the portio vaginalis cervicis in a given case; however, the blank for the cap is selected so that the shell peripheral edge, i.e., shell periphery 35, does not extend into the fornices vaginae. Slits are cut into the skirt portion of the formed cervical cap during the final trimming operation. Preferably the slits are substantially uniformly spaced from one another and extend about 1.5 to about 5 millimeters from periphery 34, i.e., from the distal edge of the skirt portion.

Alternatively, a valved cervical cap can be first formed using a blank of substantially uniform thickness substantially as disclosed in the aforementioned patent application U.S. Ser. No. 108,319, and then a flexible skirt portion can be affixed thereto in the form of an elastomeric band that is bonded to the shell portion of the cap at the shell periphery by heat welding, ultrasonic techniques, adhesive bonding techniques, or the like. Spaced slits are provided in the band at the distal, i.e., unattached, edge thereof before or after attachment to the shell portion, as desired. The added skirt portion can be about 3 millimeters wide, or wider, depending on the depth of the fornices. Usually a skirt portion width of about 3 to about 7 millimeters is adequate. A relatively wide skirt portion may be added during fabrication and subsequently trimmed to a desired width for optimum fit. As pointed out hereinabove, the slits in the skirt portion can be spaced about 2 millimeters to about 10 millimeters apart, preferably about 4 to about 6 millimeters apart, and are at least about 1.5 millimeters long.

In addition to the blanks illustrated in FIGS. 3, 4A and 4B, a cervical cap embodying the present invention can also be fabricated using a blank of the type shown in FIGS. 9, 10 and 11. Referring to these latter FIGURES, circular blank 90 comprises an elastomeric web 91 that overlies and is secured to underlying planar thermoplastic, elastomeric sheet 93. If desired, elastomeric web 91 may also have a rectangular configuration, a polygonal configuration, or the like, as long as the margins of web 91 extend beyond sheet 93. As best seen in FIGS. 10 and 11, planar sheet 93 is circular and is provided with central aperture 95 having rounded or beveled edges. The outer peripheral margin 94 of planar sheet 93 is also beveled radially outwardly and away from web 91 so as to provide a relatively smooth transition between the downwardly depending skirt portion 102 of elastomeric web 91 and planar sheet 93 when blank 90 is transformed to a cap shape as described hereinabove.

Elastomeric web 91 is intermittently bonded or otherwise secured to planar sheet 93 so as to define therebetween a channel or a plurality of channels communicating with aperture 95 and periphery 103 of planar sheet 93. In other words, elastomeric web 91 is not continuously bonded to planar sheet 93 at periphery 103; however, there may be a plurality of spaced spot or linear bonding sites, if desired. In any case, the bonding sites are selected so as to provide a one-way passageway for fluids entering aperture 95 and exiting at periphery 103 as well as to provide a one-way valving action as a result of coaction between elastomeric web 91 and the portion of sheet 93 defining aperture 95.

One-way valving action is further enhanced by providing web 91 with integral protuberance 97 that extends at least partially into aperture 95 and sealingly abuts the aforementioned portion of sheet 93 that defines aperture 95 while permitting the opening of aperture 95 in response to a fluid pressure increase within the formed cap. Protuberance 97 can be made unitary with web 91.

To facilitate registry between web 91 and sheet 93 when composite blank 90 is assembled, one or more nipples such as nipple 98 may be provided on web 91 and corresponding complementary cavities such as cavity 96 in sheet 93.

The materials of construction for the elastomeric web and for the planar sheet, as well as their thickness ratios, can be the same as those discussed hereinabove in connection with the other embodiments of this invention. Preferably the thickness of the elastomeric web is about 0.1 to about 0.4 millimeters, more preferably about 0.2 to about 0.3 millimeters. The thickness of the planar sheet preferably is about 0.6 to about 2 millimeters, more preferably about 1 to about 1.5 millimeters. For blank 90, the diameter of circular, planar sheet 93 can be about 15 millimeters to about 50 millimeters, preferably about 25 millimeters to about 40 millimeters, depending on the desired size and depth of the cervical cap to be fabricated. The relative thicknesses of the web and the sheet alsao depend to some extent on the durometer hardness value of the particular material that is utilized. In general, the softer the material the greater can be the thickness of the web and/or the sheet.

A fabricated cervical cap embodying the present invention is shown in FIG. 12. The shell portion of the cap 99 defines a concave inner surface of the cap and is entirely covered by elastomeric web portion 104 which defines the convex outer surface of cap 99. While the slits situated in skirt portion 102 in a spaced relationship to one another and extending into cap 99 from cap peripheral edge 100 can be substantially straight linear cuts, preferably these slits have an inverted-V configuration as illustrated by slits 101. In this particular embodiment skirt portion 102 is unitary with web portion 104.

The foregoing disclosure and the accompanying drawings are intended as illustrative and are not to be construed as limiting. Still other variations within the spirit and scope of the present invention as defined by the claims are possible and will readily present themselves to those skilled in the art.

We claim:

1. A blank for a removable cervical cap which comprises
a substantially planar sheet of a thermoplastic elastomeric material defining a central aperture therein; and
an elastomeric web superposed over said aperture;
said elastomeric web having a thickness less than the thickness of said sheet and being secured to said sheet about said aperture but providing a one-way passageway from said aperture between the web and said sheet; and
said blank having a margin of a thickness that is less than the thickness of said sheet in the region thereof defining said central aperture.

2. The blank in accordance with claim 1 wherein said elastomeric web is of the same material as said sheet.

3. The blank in accordance with claim 1 wherein internal edge of said region defining said aperture is beveled on the side adjacent to said web.

4. The blank in accordance with claim 1 wherein a tactile marker means is provided on said blank.

5. The blank in accordance with claim 1 wherein said planar sheet and said elastomeric web are made of styrene/elastomer block copolymers.

6. The blank in accordance with claim 1 wherein said planar sheet has a Shore A durometer hardness value of about 35 to about 70.

7. The blank in accordance with claim 6 wherein said planar sheet has a Shore A durometer hardness value of about 45 to about 60.

8. The blank in accordance with claim 1 wherein said sheet is substantially transparent.

9. The blank in accordance with claim 1 wherein said thermoplastic elastomeric material inhibits sperm motility.

10. The blank in accordance with claim 1 wherein said web is provided with a unitary protuberance that extends into said aperture.

11. The blank in accordance with claim 1 wherein said web is thicker in the region of said aperture.

12. The blank in accordance with claim 1 wherein said planar sheet has an embossed region defining said central aperture and a planar region relatively thinner than the embossed region and surrounding the embossed region.

13. The blank in accordance with claim 12 wherein the sum of the thicknesses of said sheet and said web in the embossed region covered by said web is substantially the same as the thickness of said sheet in the blank region not covered by said web.

14. The blank in accordance with claim 12 wherein the thickness ratio of said embossed region to said web is about 5:1, respectively.

15. The blank in accordance with claim 14 wherein said embossed region is about 1.5 millimeters thick.

16. The blank in accordance with claim 12 wherein said web is provided with a marker indicating location of said aperture.

17. The blank in accordance with claim 12 wherein said substantially planar sheet is a laminate of two dissimilar thermoplastic elastomeric materials and wherein said planar region surrounding said embossed central region is constituted by only one of said two dissimilar thermoplastic elastomeric materials.

18. The blank in accordance with claim 1 wherein said elastomeric web covers said planar sheet and extends beyond the periphery of the planar sheet.

19. The blank in accordance with claim 18 wherein said elastomeric web is intermittently attached to said planar sheet about the central aperture.

20. The blank in accordance with claim 18 wherein said elastomeric web is provided with an integral protuberance that extends into said central aperture.

21. The blank in accordance with claim 20 wherein said elastomeric web is additionally provided, on the same side as said protuberance, with a unitary nipple off-set from said protuberanace, wherein said planar sheet is provided with a cavity complementary to said nipple, and wherein said nipple is received within said cavity.

22. The blank in accordance with claim 18 wherein said planar sheet has a circular configuration.

23. The blank in accordance with claim 18 wherein said elastomeric web and said planar sheet both have a circular configuration.

24. The blank in accordance with claim 18 wherein said planar sheet is provided with a peripheral margin that is beveled radially outwardly and away from said elastomeric web.

25. The blank in accordance with claim 18 wherein said elastomeric web is provided with an integral protuberance extending into said central aperture and wherein the central aperture is defined by a beveled edge providing an annular contact surface contiguous with said protuberance.

* * * * *

UNITED STATES PATENT OFFICE
CERTIFICATE OF CORRECTION

Patent No. 4,369,219          Dated January 18, 1983

Inventor(s) Robert A. Goepp, Uwe E. Freese and Marvin P. Loeb

It is certified that error appears in the above-identified patent and that said Letters Patent are hereby corrected as shown below:

Col. 7, line 17, "vertical" should be -- vagina --.

Col. 7, line 28, "shell 42," should be -- shell 22, --.

Signed and Sealed this

Fifteenth Day of March 1983

[SEAL]

Attest:

GERALD J. MOSSINGHOFF

Attesting Officer     Commissioner of Patents and Trademarks